United States Patent [19]

Razaq et al.

[11] Patent Number: 5,085,760
[45] Date of Patent: Feb. 4, 1992

[54] ELECTROCHEMICAL GAS SENSORS

[75] Inventors: Mohammed Razaq, Hacienda Heights; Atulbhai S. Shah, San Dimas; Harold W. Pust, Huntington Beach, all of Calif.

[73] Assignee: Teledyne Industries, Inc., Los Angeles, Calif.

[21] Appl. No.: 563,811

[22] Filed: Aug. 6, 1990

Related U.S. Application Data

[63] Continuation of Ser. No. 404,680, Sep. 8, 1989, abandoned.

[51] Int. Cl.$^5$ .............................................. G01N 27/26
[52] U.S. Cl. ................................... 204/431; 204/432; 204/153.1
[58] Field of Search ..................... 204/431, 432, 153.1

[56] References Cited

U.S. PATENT DOCUMENTS

| | | | |
|---|---|---|---|
| 4,042,464 | 8/1977 | Blurton et al. | 204/153.1 |
| 4,052,268 | 10/1977 | Blurton et al. | 204/153.14 |
| 4,073,698 | 2/1978 | Blurton et al. | 204/153.16 |
| 4,127,462 | 11/1978 | Blurton et al. | 204/412 |
| 4,166,775 | 9/1979 | Bruckenstein et al. | 204/153.16 |
| 4,326,927 | 4/1982 | Stetter et al. | 204/153.1 |
| 4,639,306 | 1/1987 | Tomasovic et al. | 204/432 |

FOREIGN PATENT DOCUMENTS 2535401  2/1977  Fed. Rep. of Germany .

*Primary Examiner*—John Niebling
*Assistant Examiner*—Bruce F. Bell
*Attorney, Agent, or Firm*—Edward J. DaRin

[57] ABSTRACT

An electrochemical gas sensor having a high surface area gas diffusing electrode defined for diffusing gases to be sensed to reach the catalyst surfaces of the electrode to provide the cathodic reduction of oxygen in a gas mixture undergoing sensing thereat. The sensor is adapted to sense trace levels of reactive gases in parts per billion. The sensor provides for ready purging of reactive gases from the electrolyte solution for the cell. The cell is essentially insensitive to the rate of flow of gas delivered to the cathode electrode and the minor mechanical stirring of the electrolyte solutions leading to output signals of improved signal-to-noise ratios more accurately signalling the concentrations of reactive gases, such as oxygen in gas mixtures.

16 Claims, 1 Drawing Sheet

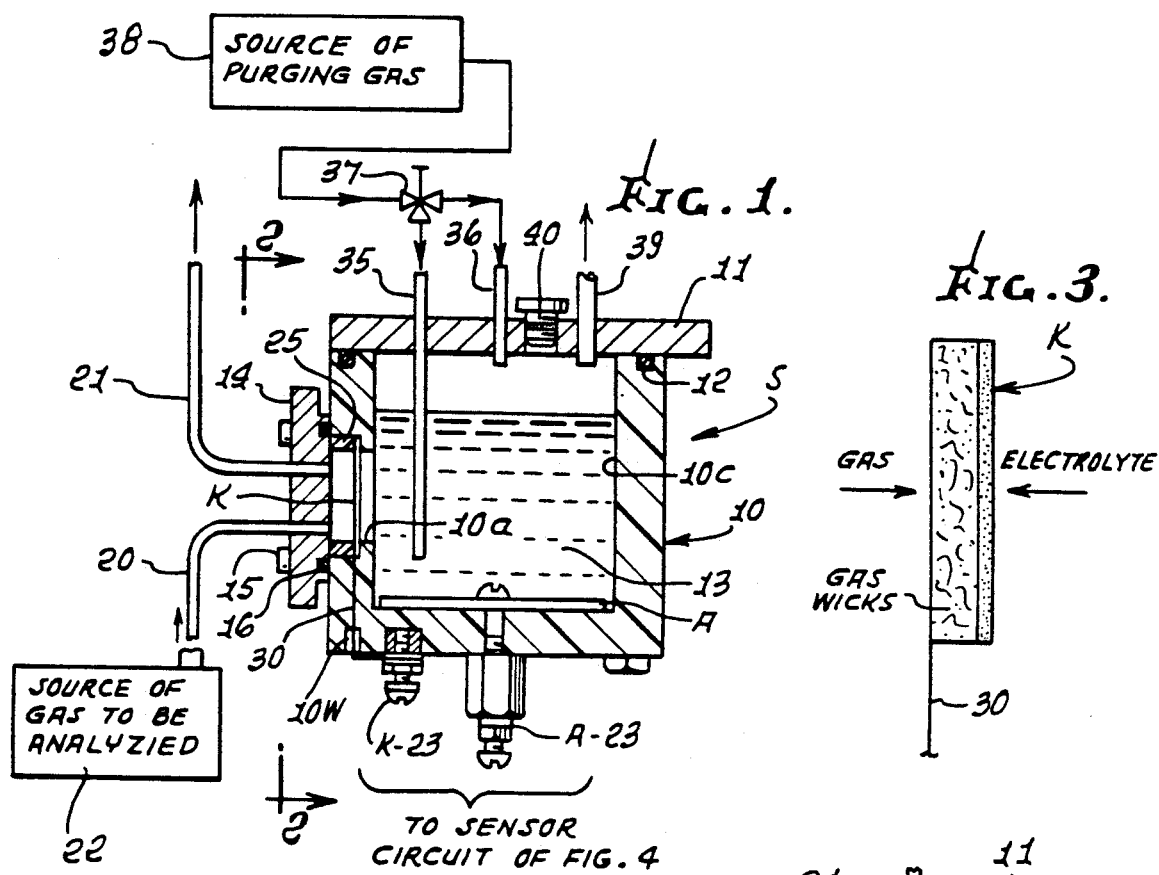
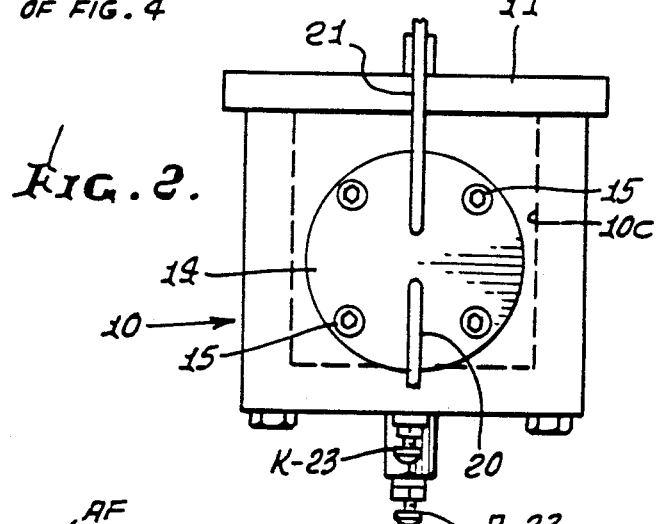
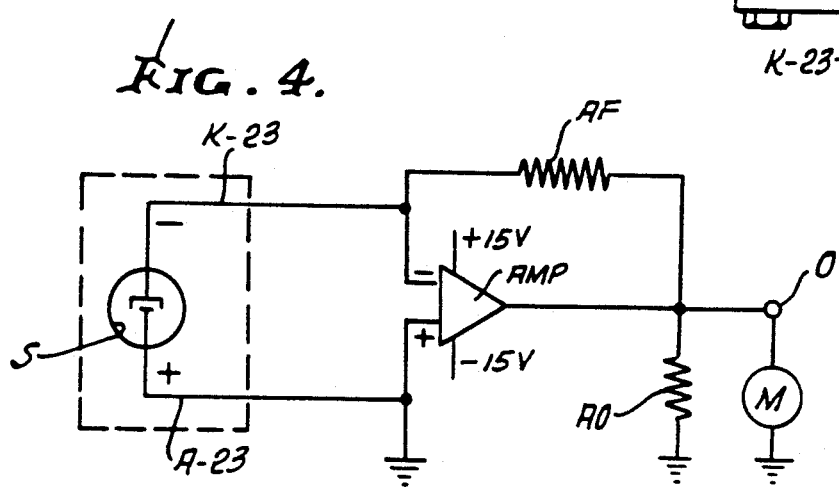

ELECTROCHEMICAL GAS SENSORS

This application is a continuation, of application Ser. No. 404,680, filed Sept. 8, 1989, now abandon.

FIELD OF INVENTION

This invention relates to electrochemical gas sensors for electrically signalling the concentration of an electrochemically active gas, such as oxygen, in a gas mixture and, more particularly, to improvements in the structural organization of the electrochemical sensing cell and an improved electrode configuration for use in such sensing cells.

BACKGROUND OF INVENTION

Electrochemical gas analyzers of the type under consideration in this invention are well-known in the art and are exemplified by the disclosures in U.S. Pat. Nos. 3,767,552 and 4,077,861. These gas analyzers are in the form of electrochemical cells that are used as sensors for determining and electrically signalling the concentration of an electrochemically active gas in a gas mixture. The gas mixture may be air and since air includes oxygen, the sensing cell determines the oxygen concentration in the gas mixture or air. For this purpose, the electrochemical cell is generally defined with anode and cathode electrodes immersed in an electrolyte for producing an electrical output signal from the sensing cell representative of the quantity of concentration of the electrochemical active gas in the sensed gas mixture. These electrochemical cells as recognized in the prior art, are characterized as either galvanic cells or polarographic cells. Generally the galvanic cell results from the selection of an appropriate active anode material, such as lead, for causing a reaction at the cathode electrode with the gas undergoing analysis leading to the derivation of an electric output current from the cell representative of the concentration of the sensed gas and applied to a suitable sensing device connected to the sensing cell. A polarographic electrochemical cell results from the selection of silver, for example, as an anode electrode and applying a small polarizing voltage between the cathode and the anode electrodes to produce the desired cathodic reaction.

There are available in the marketplace at the present time various types of electrochemical sensors for sensing oxygen, for example, based on galvanic and potentiostatic principles which are utilized for determining oxygen concentrations with great accuracy over a wide range of concentrations ranging from 1 ppm (parts per million) to 100 percent oxygen without any problem. The measurements of gas concentration, such as oxygen concentrations at trace levels which are considered in the range of 1 to 100 ppb (parts per billion), is very difficult and has not been satisfactorily solved by the workers in the art. The problems associated with such sensing devices for sensing such low levels of oxygen or other electroactive gas concentrations is complicated by the very low level of signal output that is derived from the present day sensing cells and by the electronic signal-to-noise ratio generated by the presently available electronic circuitry makes the processing of such output signals very difficult. The presently available sensors also inhere the problem of the effective removal of any dissolved oxygen in the electrolyte solution for the sensing cell, and which removal procedure has been proven to be difficult and also requiring a long period of time to minimize the dissolved oxygen in the electrolyte. The residual oxygen dissolved in the electrolyte solution for such sensors therefore interferes with the correct sensing and measurement of the oxygen in a gas mixture. These problems are greater factors when the gas to be analyzed contains only a few parts per billion, ppb, of oxygen, or the like, of electrochemically active gas.

It is of course recognized that the output signal provided by such an electrochemical sensor may in principle be increased by simply increasing the effective area of the sensing cathode electrode. When the area of the sensing cathode electrode is increased, it requires a relatively large volume of electrolyte to wet the large cathode electrode. The removal of oxygen from a large volume of electrolyte becomes extremely difficult and time consuming. This, then, severely restricts the overall size of any electrochemical oxygen sensor. At the present time when oxygen is dissolved in the electrolyte solution of such a sensor, it can be removed by either purging the electrolyte solution by an ultra pure inert gas or by an electrochemical reduction mechanism, or the combination of the two procedures. These procedures usually require several days to remove the dissolved oxygen from the electrolyte and once the undesired gas is purged from the electrolyte solution, the electrochemical sensor still has to be calibrated by means of a sample gas with a known concentration of oxygen, or of the gas to be sensed. During the calibration process, some of the oxygen or other gas again dissolves in the electrolyte which has to be removed before using the gas analyzer to provide accurate results in analyzing a gas mixture having an unknown concentration of oxygen or the like. The amount of oxygen which dissolves in the electrolyte solution during calibration depends upon the extent to which the electrolyte is exposed to the calibration gas.

Another significant problem that is known in the art with respect to currently available gas sensors is that they generally exhibit a sensitivity to either the changes in the rate of flow of the gas undergoing analysis or to mechanical vibrations due to the vibration of the supporting surface for the cell causing stirring of the electrolyte, or to both. Any changes in the rate of flow of the gas undergoing analysis and the mechanical vibrations, both influence the rate of mass transport of the dissolved electrochemically active gas to the catalyst surface and, therefore, influences the accuracy of the output signal from the electrochemical cell. This requires the precise control of the rate of flow of the gas mixture and a vibration free supporting surface for the electrochemical cell for producing accurate measurements of the gas concentrations in a gas mixture.

At the present time, semiconductor devices have been extensively used in electronic circuits, including electronic circuit boards. The use of semiconductor devices is continuously increasing. During the fabrication of the semiconductor devices, ultrapure, inert gases are required for blanketing the semiconductor devices. It has been found that any oxygen in the blanketing gases is a major contaminent of the semiconductor devices and poses a significant problem in the fabrication of such semiconductor devices. The yield in the fabrication of such semiconductor products is adversely affected by the oxygen present in the inert blanketing gas. The semiconductor fabricators, therefore, deem it essential to accurately monitor the very low levels of oxygen concentration present in the blanketing gas during the fabrication process. To achieve this aim, accurate oxygen analyzers with sensitivities in the range of 0 to 100 ppb (parts per billion), are required. The presently available oxygen sensors do not lend themselves readily to measure oxygen in this very low range. The present status of the art is that most of the electrochemical sensors useful for analyzing gas mixtures having less than 10 ppm of oxygen contain an aqueous electrolyte solution. Present day electrochemical cells function to cause the reactant gas, such as oxygen, to be first dissolved in the electrolyte solution and then it diffuses to the cathode surface and then is electrochemically reduced at the cathode electrode surface, causing an electronic current to flow, producing oxidation at the anode electrode and a current flow into the external sensing circuit that is connected between the cathode and the anode electrodes of the electrochemical sensor. The rate of flow of electric current can be easily measured, and since it is proportional to the concentration of oxygen present in the gas mixture, signals the sensed concentration.

In addition, the aforementioned problems of the prior art sensors in ordinary usage, are even more critical when an attempt is made to utilize these sensors for measuring oxygen in the range of 0 to 100 ppb. Also, the gases to be analyzed are generally very dry and, therefore, the water in the aqueous electrolyte solution is continuously lost in the form of water vapor in the use of the electrochemical cells of the prior art. Since most of the electrochemical cells are sensitive to the amount of water in the cell, it has been found necessary to humidify the gases prior to introducing them to the sensing cell, in order to minimize the loss of water from the sensing cell. Accordingly, there is a present need in the art for an improved, accurate, electrochemical cell capable of measuring concentrations of electrochemically active gases in a gas mixture and, in particular, oxygen, in the range of 0 to 100 ppb and one that is simple to construct and use and has a capability of readily removing any dissolved electrochemically active gases from the aqueous electrolyte and does not need sample gas humidification.

SUMMARY OF INVENTION

The present invention provides an improved, inexpensive and accurate electrochemical gas analyzing, sensing cell that is capable of sensing concentrations of electrochemically active gases in gas mixtures, such as oxygen, in the range of 0 to 100 ppb and eliminates most of the aforementioned problems of prior art devices. The electrochemical gas analyzing sensor of the present invention utilizes a high surface area, metal catalyzed gas diffusion electrode as the sensing cathode that causes the electrochemical reaction to occur directly at the electrode surface and provides a significant increase in the electrical output current from the sensing cell per geometric area of electrode. Due to the increased output current produced by the sensing cell, the signal-to-noise ratio is increased and, as a result, the electronic sensing and measuring circuit coupled to the sensor is simplified. In accordance with the present invention, the gas to be analyzed is circulated to the back of the cathode electrode of the electrochemical cell to cause it to diffuse through the microporous structure of the backing layer so as to arrive at the catalyst metal dispersed on the electrode surface exposed to the electrolyte. As a result of much higher activity of the catalyst due to the high surface area of the catalyst, very little of the gas undergoing analysis, such as oxygen, will pass directly through the catalyst layer unreacted and, therefore, a minimum amount of the reactant gas will be dissolved in the bulk of the electrolyte, thereby increasing the accuracy of the sensing device. The design of the improved sensor is such that the sensitivity is not seriously affected by the loss of a large amount of water from the aqueous electrolyte solution utilized in the cell and, therefore, eliminates the need for humidifying the gas. In addition, the sensor is insensitive to minor mechanical vibrations and to the gas flow rate, provided the pressure of the gas undergoing analysis as applied to the cathode electrode does not change with the flow rate.

From the standpoint of removing any dissolved oxygen or similar active gas from the aqueous electrolyte solution, this can be accomplished more efficiently with the present invention by bubbling pure nitrogen through the electrolyte solution to cause the desired reaction for quickly removing the oxygen from the electrolyte solution. Once the electrolyte solution is free from dissolved oxygen, the same basic means can be employed to cause a nitrogen stream to flow over the surface of the electrolyte, thereby minimizing the loss of water from the cell due to evaporation. Once the sensing operation is complete, nitrogen gas can again be bubbled through the electrolyte solution to remove any trace amounts of oxygen that may have been dissolved during the sensing operation. This will allow the cell to be immediately ready to analyze a new gas sample with a significantly lower oxygen concentration in a relatively short period of time after the last use thereof.

From a broad structural standpoint, the electrochemical sensing cell of the present invention comprehends the use of a cathode electrode capable of use with low concentrations of reactive gases in the parts per billion range, generally characterized as a high surface area metal catalyzed gas diffusion electrode having an electrically conducting, hydrophobic, porous Teflon-carbon backing layer bonded to a relatively thin layer of high surface area metal catalyst dispersed on a high surface area conductive support permitting the catalyst to be wet when exposed to an electrolyte, and whereby the gas mixtures conveyed through the hydrophobic layer to the catalyst area, cause reaction thereat of the electrochemically reactive gas undergoing sensing upon the exposure of the porous layer to a gas mixture and yet preventing the electrolyte from flowing outwardly of the electrochemical sensing cell beyond the catalyst layer of the electrode. The catalyst is covered with a very thin layer of the electrolyte, and the gas to be analyzed reaches the catalyst surface relatively quickly.

From the standpoint of the structural organization of the electrochemical sensing cell, the present invention comprehends an electrically insulative container having an aperture in one side of the side wall thereof mounting cathode electrode means to expose only the catalyst surface of the cathode electrode means to the electrolyte solution therein. The anode electrode means is also supported within the container along with the fluid electrolyte for wetting the anode electrode means and the exposed surface of the cathode electrode means. The cathode electrode means is constructed and defined as a composite structure with a high surface area catalyst and a gas diffusing, hydrophobic backing layer arranged on the opposite side of the electrode. The backing layer is adapted for conveying gas therethrough to a catalyst metal layer having a high surface area adapted to be wet by the electrolyte to cause the electrochemically active gas, such as oxygen, to react thereat. The hydrophobic surface blocks the flow of electrolyte beyond the catalyst layer of the electrode. The sensor includes means for continuously circulating a gas mixture to be analyzed for exposure to the gas diffusing back layer of the cathode electrode means to be diffused therethrough to the catalyst layer to be reacted thereat with a minimum amount of unreacted dissolved gas to pass through the catalyst layer into the bulk of the electrolyte, thereby providing an electrical current flow between the cathode means and the anode means through the external circuit proportional to the sensed concentration of the reactive gas in the mixture.

BRIEF DESCRIPTION OF THE DRAWINGS

These and other features of the present invention may be more fully appreciated when considered in light of the following specification and drawings, in which:

FIG. 1 is a cross-sectional, front view of an electrochemical cell embodying the present invention;

FIG. 2 is a side elevational view of the electrochemical sensing cell of FIG. 1, taken along the line 2—2 of FIG. 1;

FIG. 3 is an enlarged diagrammatic illustration of the side of the cathode electrode utilized in the cell of FIG. 1; and FIG. 4 is an electrical, schematic diagram of a sensing circuit for use with the electrochemical cell of FIG. 1.

DETAILED DESCRIPTION OF THE PREFERRED EMBODIMENT

Now referring to the drawings, the electrochemical sensing cell S of the present invention will be described in detail. The sensing cell S is illustrated in the drawings and will be described as a sensing cell based on galvanic operation as a result of the choice of an active anode material for use in the electrochemical sensing cell. It will be recognized by those skilled in the art that such sensing cells may also be readily adapted to function as potentiostatic and polarographic sensors and sensors which function on oxidation as well as reduction of the chemical reactants.

The sensor S is housed in a generally, electrically insulative housing 10 that may be constructed of an electrically insulative plastic material, such as an acrylic plastic. The housing 10, as illustrated, has a generally U-shaped configuration with an open top end and which open end is secured by a cover member 11 which may be a stainless steel member that is sealed to the insulative housing 10 proper, including by means of the O-ring 12, as illustrated. One side wall of the housing 10, the left hand wall, is provided with a circular aperture 10a for mounting a cathode electrode K therein for exposure to an electrolyte solution 13. The housing 10 has an internal cavity 10c for storing the electrolyte solution 13. The cavity 10c for the housing 10 also mounts a circular anode electrode A, illustrated as overlying the bottom inside wall of the sensor S. The aperture 10a in the side wall of the housing 10 is enclosed by a circular cover element 14 that is secured to the housing 10 proper in a conventional fashion by means of a plurality of fasteners 15 spaced around the periphery of the circular element 14. The aperture 10a is sealed by the provision of an O-ring 16 secured between the outer wall of the container 10 and the inner wall of the element 14 at the defined shoulder. The cover member 14 is provided with a pair of spaced apertures thereon for receiving a pair of gas tubes for conveying the gas to be analyzed past the back side of the cathode electrode K and then is conveyed outside of the container 10. For this purpose, a gas inlet tubular element 20 is arranged to distribute gas near the bottom of the aperture 10a for conveying the gas to be analyzed into the aperture 10a for traversing the adjacent backing layer of the cathode K. A gas exit tubular element 21 is arranged upwardly of the opening 10a for receiving a gas moving past the cathode K and conveying the gas by means of the tube 21 outside of the sensor S. The source of gas to be analyzed is illustrated in block form in FIG. 1 and is identified by the reference numberal 22. The source 22 has a tubular element that is normally coupled for delivering gas to the tubular element 20 for analysis by the sensor S. The bottom wall of the sensor S secures an external cathode terminal K-23 and an external anode terminal A-23 that are electrically connected to the corresponding cathode K and anode A electrodes within the sensor S proper, as will become more evident hereinafter.

An important consideration of the present invention is the utilization of a novel cathode electrode K in the sensor S that is generally characterized as a high surface area metal catalyst gas diffusion electrode. Electrodes that are characterized and utilized in the present invention are commercially available from Prototech Company of Newton, Mass., and other suppliers. Specifically, the structural organization of such an electrode is well-known for use in fuel cells and is disclosed in detail in U.S. Pat. No. 4,647,359 and assigned to said Prototech Company. The commercial embodiments of such electrodes as disclosed in the Prototech patent are available from the Prototech Company and useful in the sensor S. The presently preferred embodiment of the electode that is commercially available is identified as a gas diffusing electrode on Toray paper and has been utilized in the sensor S. The disclosure of U.S. Pat. No. 4,647,359 is incorporated herein by reference. Although such electrodes are utilized in fuel cells for generating electrical power, there is no known utilization of such electrodes in electrochemical gas analyzers of the type which is the subject of the present invention and, particularly, in sensing oxygen traces in the parts per billion range. The use of a high surface area metal catalyzed gas diffusion electrode affords the possibility of achieving much higher effective surface areas for the sensing cathode electrode of an electrochemical gas analyzing cell without increasing its geometric area. The typical effective surface area of a gas diffusion electrode is usually 100 times greater than its geometric area, when compared to a smooth, metal screen electrode where the effective area is usually twice the geometric area.

For the purposes of the present invention, the basic characteristics and structural organization facilitating the understanding of the gas diffusion cathode K will be explained in conjunction with the diagrammatic representation in FIG. 3 of the composite structure defining the gas diffusing cathode K. The cathode K is a composite structure having a gas diffusing polytetrafluoroethylene-carbon backing layer on one side thereof bonded to a relatively thin layer of high surface area catalyst metal dispersed on a high surface area carbon support; see FIG. 3. The gas diffusing portion of the cathode K is illustrated to the left in FIG. 3 and consists of a microporous structure of polytetrafluoroethylene and carbon mixture. The microporous structure functions as gas wicks to convey the gas subjected thereto through the microporous, electrically conductive, hydrophobic structure of the polytetrafluoroethylene-carbon mixture to the catalyst surface. This gas receiving and diffusing layer permits the conveyance of the gas therethrough by means of the gas wicks formed by polytetrafluoroethylene-carbon structures. The catalyst layer of the cathode is a relatively thin layer having approximately 1/10th of the thickness of the backing layer. This layer can be termed the catalyst layer as it is exposed to the electrolyte solution in the cell S. The catalyst layer consists of a high surface area metal catalyst, such as silver, platinum, gold and the like metals, dispersed on a high surface area carbon support. A relatively small amount of polytetrafluoroethylene or a polymeric, fluorinated hydrocarbon material is used as a binder of the metallic catalyst to the carbon support. The backing layer is also characterized as being a hydrophobic porous layer which permits the gas to be analyzed to be conveyed therethrough to the catalyst layer but blocks or prevents the electrolyte solution from traveling beyond the catalyst layer and thereby exiting the sensor S. The cathode electrode K has a circular configuration and the presently preferred embodiment has an area of approximately 1 square inch. The thus defined gas diffusing backing layer of the sensing cathode K allows the gas to be analyzed to diffuse through i&s microporous structure and reach the metallic catalyst surfaces where the electrochemically active gas, such as oxygen, reacts. Since the gas to be analyzed is diffused through the gas wicks of the backing layer, only the electrolyte immediately adjacent the catalyst metal surface is exposed to the gas. As a result of the very high effective surface area of the catalyst provided for the cathode K, most of the reacting gas is consumed at the cathode K surface. It is thought that only a small portion of the unreacted dissolved gas passes through the catalyst layer to the bulk of the electrolyte 13 which allows it to be rapidly removed, as will be explained hereinafter.

Referring back to the sensor structure of FIG. 1, it will be seen that the cathode K is mounted in the circular cavity 10a on the side wall of the sensor housing 10, as illustrated. For this purpose, the cathode K is held in position by means of an insulative, holding ring which may be a plastic polyethylene ring and is identified by the reference numeral 25. The polyethylene ring is mounted between the outer surface of the housing 10 and the outer surface of the cathode K, as best illustrated in FIG. 1. Along with the holding ring 25, a very thin silver ring (not shown) is arranged between the outer surface of the cathode K and the insulative ring 25. The silver ring is in electrically conducting contact with the cathode electrode K. A number of electrical lead wires, thin silver wires, are connected between the conductive silver ring and the external cathode terminal K-23, although only one lead wire 30 is illustrated.

The one lead wire 30 is electrically connected to the silver ring and is passed through a suitable aperture in the inside of the side wall of the housing 10 and through an enlarged aperture 10w to extend outside the lower end of the housing 10. The outer end of the silver wire 30 is electrically connected to the external cathode terminal K-23, as illustrated. The cover member 14 for the sensor S is mounted so that the distance between the outside surface of the gas exposed layer of the cathode K and the inside wall of the plate 14 is typically greater than ½ inch. The gas to be analyzed is conveyed from the source 22 through the tubular conduit 20 and enters the space between the cathode K and the inside surface of the plate 14 and after being subjected to the cathode, the remaining amount of gas exits from the second tubular element 21 secured to the plate 14. During the process, the gas to be analyzed contacts the backing surface of the cathode K and diffuses through the gas wicks provided to arrive at the catalyst surface of the electrolyte layer. A typical surface area of the catalyst metal is 150 $m^2/g$. The gas to be analyzed is circulated past the backing layer of the cathode K at atmospheric pressure and it is preferred to be maintained at such a pressure. The rate of diffusion of the gas through the gas wicks of the backing layer for the cathode K is insensitive to the rate of flow of the gas exposed to the backing layer provided the gas pressure remains substantially unchanged. Therefore, variations in the gas flow rate will not affect the electrical signal output from the sensor S. In addition, minor mechanical vibrations causing stirring of the electrolyte solution will not affect the integrity of the electrical output signal from the sensor S since the gas mass transport occurs through the diffusing cathode electrode and not the electrolyte solution, as in the prior art sensors discussed hereinafter. This mounting arrangement of the cathode electrode K substantially limits the contact of the electrolyte solution to the gas mixture undergoing analysis.

The anode electrode A, which may be either constructed of lead, cadmium or the like, is a circular disc mounted on the inside bottom wall of the cavity 10c for the housing 10. An electrically conductive stud 31 is connected onto the bottom side of the anode wall of the housing 10 and is electrically connected to an external anode terminal A-23 and secures the anode electrode to the housing 10.

The open end of the housing 10 is sealed by means of a stainless steel plate 11 having three apertures for accommodating three stainless steel tubular elements that are welded thereto. The left hand tubular element, as illustrated in FIG. 1, is identified by the reference numeral 35 and extends upwardly or outwardly of the plate 11 and downwardly into the electrolyte solution 13 for the sensor S. The tubular element 35 may have a fine pore glass frit attached thereto for bubbling a purging gas into the electrolyte solution 13. When a frit is utilized, the length of the frit stem is defined so that the gas emerges near the bottom of the electrolyte solution. For this purpose, the stem of the frit may have a disc at its end for dispersing the purging gas therethrough. The second tubular element 36 is spaced inwardly from the element 35 and the two tubular elements 35 and 36 are connected and controlled by means of a three-way valve 37. The tubular element 36 extends outwardly of the cover element 11 and a short distance into the space between the bottom wall of the cover 11 and the top surface of the electrolyte 13. The three-way valve 37 is connected to a source of purging gas 38, shown in block form, to receive and control the flow of the gas. The function of the three-way valve 37 is to control the flow of the purging gas into one of the tubular elements 35 and 36 and to completely turn off the gas. A third tubular element 39 that is welded to the cover 11 is a short length of tubing which extends a short distance below the bottom surface of the cover 11 and outwardly of the top of the cover and functions as a vent for exhausting the gas in the sensor S proper to the atmosphere. The sensor S is also illustrated with a water port 40 for permitting water to be added to the electrolyte solution 13. The port 40 is sealed with an O-ring and a polytetrafluoroethylene screw, as illustrated.

The aqueous electrolyte solution may be any electrolyte known in the art and in the disclosed embodiment, the electrolyte utilized was a potassium hydroxide, aqueous solution.

As mentioned hereinabove, the sensor S of the present invention is particularly adapted for sensing oxygen concentrations that are characterized as trace quantities or quantities in the range between 0 and 100 ppb. As is the usual practice, in order to assure correct output readings from a sensor, the electrolyte solution 13 must have the dissolved oxygen removed therefrom prior to analyzing a gas. In accordance with the present invention, one method of purging the reactive gases from the electrolyte solution is by the provision of the source of purging gas 38, which may be pure nitrogen, which is bubbled through the electrolyte solution 13 by operating the valve 37 to apply the nitrogen gas from the source 38 directly into the electrolyte solution, as illustrated. This can rapidly remove the oxygen from the electrolyte. Once the electrolyte 13 is free of dissolved oxygen, the sensor S is ready to analyze the gas mixture coupled thereto. During the sensing period, the valve 37 may be controlled to cause the nitrogen gas from the source 38 to be removed from the tubular element 35 and coupled to the tubular element 36. This will cause the nitrogen gas to flow over the top surface of the electrolyte 13 during the analysis period. By passing the nitrogen gas over the electrolyte 13 in this fashion, it will minimize the loss of water from the electrolyte due to the evaporation and improve the overall operation of the sensor S.

In the analysis of the gas to be analyzed, the source 22 is coupled to the inlet conduit 20 so as to circulate it past the backing layer of the cathode K to permit it to diffuse through the backing layer and reach the catalyst metal where it reacts. An important consideration in this reaction procedure should be noted at the present time. In prior art sensors, the gas to be analyzed is first caused to be dissolved in the aqueous electrolyte solution and once the gas is dissolved, it diffuses towards the cathode electrode through a relatively thick layer of electrolyte, and once it reaches the electrode, is reduced at the electrode-electrolyte interface. Only a fraction of the dissolved gas reacts at the electrode and a substantial amount of the reactive gas stays in the bulk electrolyte. This is in contrast to the present invention where most of the dissolved reactive gas is used up at the high surface area electrode covered by a thin film of electrolyte without diffusion into the bulk electrolyte.

The cathode electrode K, as in the prior art, functions as the sensing electrode and when oxygen is being sensed, the sensed oxygen produces a cathodic current at the catalytic metal surface in response to the wetting of the metal and the reception of the gas mixture undergoing analysis thereat, and the cathodic reaction provides an electric current flow externally between the cathode K and the anode A and the anode is oxidized in response to the cathodic reduction. The external electric current, then, is available at the terminals K-23 and A-23 on the outside of the sensor S.

Now referring to FIG. 4, the electrical circuit for processing the electrical signals derived from the sensing cell S at the external cathode terminal K-23 and the external anode terminal A-23 will be explored. For this purpose, it should be noted that the output current available at these external terminals is on the order of 10 to 14 microamperes per parts per million of oxygen in a gas to be analyzed when the cathode electrode has the aforementioned one inch square diameter. This electrical output is about ten times higher than the conventional oxygen analyzers presently known for sensing the low oxygen concentrations in gas mixtures. Any conventional sensing circuit may be employed by coupling it to the external anode and cathode terminals and in FIG. 4, a conventional operational amplifier Amp is illustrated connected to the external anode and cathode terminals with the anode A-23 connected to the negative input terminal of the amplifier Amp. The output circuit for the amplifier Amp is connected in series circuit relationship with an output resistor AO connected to a common voltage level or ground. A feedback resistor AF is connected between the output terminal common to the resistors AR and AO, to the negative input terminal of the amplifier Amp. A meter M may be connected between the output terminal O and ground that is calibrated to read the concentration of the sensed oxygen of the gas undergoing analysis for a direct read-out of the sensor S.

We claim:

1. An electrochemical sensing cell for sensing the concentration of an electrochemically active gas including oxygen in a gas mixture including concentrations of said active gas in the parts per billion range, comprising an electrically insulative container having an aperture in one of the side walls, cathode electrode means mounted to the apertured wall of the container whereby only one surface of the electrode is exposed to the inside of the container, anode electrode means supported within the container, a fluid electrolyte adapted to be stored within the container for wetting said anode electrode means and said one surface of said cathode electrode means, said cathode electrode means being constructed and defined as a composite structure with an electrically conductive gas diffusion, hydrophobic surface arranged on the opposite side of said one surface exposed to the inside of the container and with the electrically conducting, hydrophobic, gas diffusion layer adapted for conveying gas therethrough for permitting measurements in the parts per billion range and a silver or gold catalyst with a surface area on the order of 150 square meters per gram dispersed on a carbon support and adapted to be wet by an electrolyte stored in the container to cause the electrochemically active gas conveyed through the gas diffusion surface to react at the catalyst surfaces, the hydrophobic surface blocking the flow of electrolyte outside of said catalyst surface, and means for continuously circulating said gas mixture to be analyzed for exposure to the gas diffusion surface of the cathode electrode means to be diffused therethrough to the catalyst layer so that the active gas is reacted at the catalyst surface with a minimum amount of dissolution of said active gas in the electrolyte and thereby providing an electrical current flow from said cathode means to said anode means representative of the concentrations of the sensed electrochemically active gas including in parts per billion range.

2. An electrochemical sensing cell as defined in claim 1 including means secured to the container for conveying a gas into the container for removing any reacting gas dissolved in the electrolyte, and means secured to the container for venting the container of the gas mixture under analysis.

3. An electrochemical sensing cell as defined in claim 1 or 2 including port means for adding water to the container.

4. An electrochemical sensing cell as defined in claim 1 or 2 including means secured to the container for conveying a preselected gas into the stored electrolyte for removing any reactive gas dissolved in the electrolyte prior to subjecting the cell to a gas to be analyzed, and means secured to the container for conveying a preselected gas over the top surface of the stored electrolyte, and valve means coupled to each of said means for individually controlling the flow of the preselected gas to one of said conveying means.

5. An electrochemical sensing cell as defined in claim 2 wherein said means is a tube having a fine pore glass frit attached thereto, the glass frit having a frit stem extending adjacent the bottom of the sensing cell and a frit disc attached adjacent the end of the frit stem for dispering the inert gas into the electrolyte for removing the dissolved electrochemically active gases from the electrolyte solution.

6. An electrochemical cell comprising an insulative container, a cathode electrode mounted to a wall of said container whereby only one surface of the cathode electrode is exposed to the inside of the container, an anode electrode support within the container, a fluid electrolyte adapted to be stored within the container and exposed to the anode electrode and said one surface of the cathode electrode to wet said electrodes for reacting an electrochemically active gas in a gas mixture undergoing measurement subjected to the non-electrolyte surface of the cathode electrode, said cathode electrode being constructed and defined with microporous, hydrophobic structure arranged on the opposite side of the electrolyte exposed surface thereof permitting a gas mixture to be analyzed to diffuse through said microporous structure, the electrolyte exposed surface of the cathode electrode being a thin layer of a conductive support with a gold or silver metal catalyst of a surface area on the order of 150 square meters per gram dispersed on the conductive support, the catalyst layer being exposed to said electrolyte and the hydrophobic layer is exposed to the gas mixture to be analyzed, means for circulating a gas mixture to be analyzed including an electrochemically active gas such as oxygen through the container and to be conveyed and exposed to the microporous surface of the cathode electrode for permitting the gas mixture to diffuse to the catalyst layer for reaction thereat, the gas mixture including an electrochemically active gas to be sensed and reacting at the catalyst layer, a cathode terminal secured to a wall of the container and electrically connected to the cathode electrode, and an anode terminal secured to a wall of the container and electrically accessible on the outside of the container and electrically connected to the anode electrode.

7. An electrochemical cell as defined in claim 6 including electronic circuit means adapted to be connected to the cathode and anode terminals on the outside of the container to be responsive to the electrical current generated in the electrochemical cell for providing a sensing electrical signal related to the concentration of the sensed electrochemically active gas in the applied gas mixture.

8. An electrode for use in an electrochemical gas sensing cell for sensing the concentrations, including concentrations in the parts per billion range, of electrochemically active gases such as oxygen in a gas mixture, said electrode being generally characterized as a large effective surface area metal catalyzed gas diffusion electrode and comprising a conductive hydrophobic, porous gas conveying layer bonded to a relatively thin layer of a gold or silver metal catalyst with a surface area on the order of 150 square meters per gram dispersed on said support, permitting the catalyst to be wet when exposed to an electrolyte solution whereby said gas mixture is conveyed through the hydrophobic layer to the catalyst areas to cause reaction thereat of the electrochemically active gas undergoing sensing including concentrations in the parts per billion range upon the exposure of said porous layer to a gas mixture and the wetting of said catalyst surfaces.

9. An electrode as defined in claim 8 wherein the electrode comprises an electrically conductive microporous composite polytetrafluoroethylene-carbon structure constructed and defined as a gas diffusion layer to permit gas to be diffused therethrough, and the relatively thin layer of catalyst comprises a silver catalyst with a surface area on the order of 150 square meters per gram dispersed on a carbon support, bonded to said gas diffusing layer.

10. An electrode for use in an electrochemical sensing cell for sensing the concentration of an electrochemically active gas such as oxygen in a gas mixture including concentrations in the parts per billion range, said electrode comprising a composite electrode having one layer constructed and defined with a conductive hydrophobic, microporous structure of a preselected configuration permitting a gas mixture containing an electrochemically active gas to be analyzed to diffuse through said microporous structure of said one layer, and a second catalyst layer deposited over one surface of the first layer for exposure to an electrolyte, the catalyst layer being further characterized as being an electrically conductive layer bonded to said one layer for preventing the passage of any electrolyte therethrough with the electrolyte exposed surface being a relatively thin layer of large effective surface area gold or silver metal catalyst dispersed on a large effective surface area conductive support that has a relatively small geometric area with the dispersed catalyst being on the order of 150 square meters per gram whereby any oxygen in the gas mixture undergoing analysis traverses through the second layer and the electrochemically active gas is substantially all reduced at the catalyst surfaces when the catalyst is wet.

11. An electrode for sensing the concentration of an electrochemically active gas such as oxygen in a gas mixture to be analyzed upon exposure to the gas diffusion surface of the electrode including concentrations in the parts per billion range of the electrochemically active gas for use in an electrochemical sensing device, said sensing electrode being constructed and defined with an electrically conducting, hydrophobic, microporous layer for conveying said gas mixture to be analyzed through the first layer when exposed thereat, and a second layer overlying one surface of the first layer, said second layer including a relatively thin layer of a gold or silver catalyst with a surface area on the order of 150 square meters per gram dispersed on a carbon support to cause the active gas of the gas mixture conveyed through the first and second layers to be reduced at said catalytic layer when the catalyst layer is wet by an electrolyte solution, said first layer being characterized as permitting a gas mixture to be diffused through the first layer and through the second layer to permit sensing in the parts per billion range but blocking the flow of any electrolyte solution with which said electrode is wet beyond the catalyst layer thereby permitting sensing at the catalyst layer of electrochemically active gases such as oxygen including concentrations in the parts per billion range.

12. An electrode as defined in claim 11 wherein the electrode is constructed and defined for sensing very low concentrations of electrochemically active gases such as oxygen in a gas mixture including concentrations in the parts per billion range and the electrode functions as an electrode in the electrochemical sensing device, said first layer having a micropore structure of polytetrafluoroethylene-carbon mixture, wherein the porous structure functions as gas wicks for conveying gas, and the said second layer comprises a thin layer of high surface area metal catalyst dispersed on a high surface area carbon support, the second layer having a thickness that is approximately 1/10 of the thickness of the first layer.

13. An electrode as defined in claim 11 or 12 wherein the catalyst is a high are silver.

14. An electrode as defined in claim 11 or 12 wherein the catalyst is a high surface area gold.

15. A method for sensing the concentrations of an electrochemically active gas such as oxygen in a gas mixture including concentrations of such an active gas in the parts per billion range by means of an electrochemical sensing cell in an insulative container having an aqueous electrolyte solution stored in the container, including the steps of supporting a cathode electrode in the container whereby only one surface of the cathode electrode is wet by the electrolyte solution, supporting an anode electrode within the container so as to be exposed to the electrolyte within the container to thereby cause the electrochemical reaction of the gas undergoing sensing by the wet anode and cathode electrodes, the step of supporting the cathode electrode includes the step of providing a sensing cathode electrode characterized as having a microporous, hydrophobic gas diffusing layer arranged on the opposite side of the electrolyte exposed catalyst surface of the cathode electrode for permitting a gas to be analyzed to diffuse through said gas diffusing layer for permitting sensing of the electrochemically active gas in the parts per billion range, said cathode electrode having a small geometric size on the order of 1 square inch in area, the said catalyst surface of the cathode electrode being a gold or silver metal catalyst dispersed on the carbon support and bonded to said gas diffusing layer for producing an effective surface area many times the geometric size of the electrode for wetting the catalyst with an electrolyte, and distributing a gas mixture to be analyzed into the container to be exposed to and engage said gas diffusing layer of the sensing cathode electrode whereby the gas mixture diffuses through the electrode to said catalyst layer of the electrode for reaction of the electrochemically active gas at the wet catalyst surface including when the sensed gas is in the parts per billion range and thereby providing an electrical current flow between said electrodes that is a measure of the sensed electrochemically active gas.

16. A method for sensing the concentration of an electrochemically active gas as defined in claim 15 including the step of providing an electrical output signal from the sensing cell electrodes related to the concentration of the sensed electrically active gas in the gas mixture distributed to said electrode surface.

* * * * *

UNITED STATES PATENT AND TRADEMARK OFFICE
CERTIFICATE OF CORRECTION

PATENT NO. : 5,085,760

DATED : February 4, 1992

INVENTOR(S) : Mohammed Razaq et al

It is certified that error appears in the above-identified patent and that said Letters Patent is hereby corrected as shown below:

```
Column 7, line 26, delete "i&s" and insert --its--.
Column 11, line 49, after "electrically" insert -- accessible
                    to the outside of the container and
                    electrically --.
Column 13, line 19, delete "are" and insert --surface area--.
```

Signed and Sealed this

Sixth Day of July, 1993

*Attest:*

MICHAEL K. KIRK

*Attesting Officer*  *Acting Commissioner of Patents and Trademarks*